US012690875B2

(12) United States Patent
Hilton

(10) Patent No.: US 12,690,875 B2
(45) Date of Patent: Jul. 28, 2026

(54) ROTARY CUTTING TOOL AND POWERED HANDPIECE ADAPTOR ASSEMBLIES, SYSTEMS, AND METHODS OF USE

(71) Applicant: Medtronic, Inc., Minneapolis, MN (US)

(72) Inventor: Allen P. Hilton, Arlington, TX (US)

(73) Assignee: Medtronic Navigation, Inc., Lafayette, CO (US)

( * ) Notice: Subject to any disclaimer, the term of this patent is extended or adjusted under 35 U.S.C. 154(b) by 0 days.

(21) Appl. No.: 18/825,536

(22) Filed: Sep. 5, 2024

(65) Prior Publication Data

US 2024/0423642 A1     Dec. 26, 2024

Related U.S. Application Data

(62) Division of application No. 17/523,335, filed on Nov. 10, 2021, now Pat. No. 12,082,825.

(Continued)

(51) Int. Cl.
*A61B 17/16*              (2006.01)
(52) U.S. Cl.
CPC ........ *A61B 17/162* (2013.01); *A61B 17/1615* (2013.01)
(58) Field of Classification Search
CPC . A61B 17/16; A61B 17/1613; A61B 17/1615; A61B 17/1617; A61B 17/162;

(Continued)

(56) References Cited

U.S. PATENT DOCUMENTS 4,818,157 A * 4/1989 Kouvelis .............. B25D 17/005
                                                                       81/125
5,941,891 A * 8/1999 Walen ................ A61B 17/1633
                                                                       606/167

(Continued)

FOREIGN PATENT DOCUMENTS

CN           106714707 A       5/2017
CN           114642474 A   *   6/2022   ......... A61B 17/1631
WO     WO-2016199152 A1  *  12/2016   ........... A61B 17/162

OTHER PUBLICATIONS

European Office Action for related European Application No. 21214377.0; Dated: Nov. 20, 2024; 6 pages.

(Continued)

*Primary Examiner* — Eric S Gibson
(74) *Attorney, Agent, or Firm* — Harrity & Harrity, LLP

(57)                ABSTRACT
An adaptor assembly for coupling a cutting tool to a drill drive chuck such that driven rotation of the drive chuck is transferred to the cutting tool by the adaptor assembly. The adaptor assembly includes a rod, a collet and an enclosure. A proximal region of the rod provides an adaptor male coupling portion configured to engage a drill drive chuck. A leading of the collet provides an adaptor female coupling portion configured to engage a surgical cutting tool tang. Further, the rod and the collet form complementary engagement features for coupling to one another. The enclosure rotatably maintains the collet. Upon final assembly of the rod to the collet, rotation of the rod is transferred to the collet. During use, the adaptor assembly can facilitate coupling of a cutting tool to a powered handpiece under circumstances where the cutting tool is otherwise incompatible with the powered handpiece.

12 Claims, 12 Drawing Sheets

Related U.S. Application Data

(60) Provisional application No. 63/127,533, filed on Dec. 18, 2020.

(58) Field of Classification Search
  CPC ............ A61B 17/1622; A61B 17/1624; A61B 17/1626; A61B 17/1628; A61B 17/1631; A61B 17/1633; B23B 31/008; B23B 31/20
  See application file for complete search history.

(56) References Cited

U.S. PATENT DOCUMENTS

| | | | | |
|---|---|---|---|---|
| 5,993,454 | A * | 11/1999 | Longo | B23Q 5/048 606/85 |
| 6,139,228 | A * | 10/2000 | Longo | B25F 5/001 408/710 |
| 6,474,656 | B1 * | 11/2002 | Thomas | B25B 23/0035 408/239 R |
| 6,733,218 | B2 * | 5/2004 | Del Rio | A61B 17/162 408/232 |
| 7,549,992 | B2 * | 6/2009 | Shores | A61B 17/1633 606/80 |
| 7,559,927 | B2 * | 7/2009 | Shores | A61B 17/162 606/79 |
| 7,766,585 | B2 * | 8/2010 | Vasudeva | B25B 23/0035 279/22 |
| 8,939,979 | B2 * | 1/2015 | Del Rio | A61B 17/1637 606/80 |
| 9,855,060 | B2 * | 1/2018 | Ardel | A61B 17/162 |
| 10,736,642 | B2 | 8/2020 | Burke | |
| 10,849,634 | B2 * | 12/2020 | Nguyen | A61B 17/1622 |
| 10,905,453 | B2 * | 2/2021 | Cihak | A61B 17/1615 |
| 10,993,729 | B1 * | 5/2021 | Aman | A61B 17/1697 |
| 11,154,319 | B2 * | 10/2021 | Dexter | A61B 17/3205 |
| 11,364,606 | B2 * | 6/2022 | Fairchild | B25B 23/1405 |
| 12,082,825 | B2 * | 9/2024 | Hilton | B23B 31/20 |
| 2003/0023256 | A1 * | 1/2003 | Estes | A61B 17/1633 606/167 |
| 2003/0229351 | A1 * | 12/2003 | Tidwell | A61B 17/1633 606/80 |
| 2004/0081523 | A1 * | 4/2004 | Vasudeva | B23B 31/005 408/240 |
| 2005/0116673 | A1 * | 6/2005 | Carl | A61B 17/1626 318/432 |
| 2006/0259055 | A1 | 11/2006 | Thorne et al. | |
| 2007/0269280 | A1 * | 11/2007 | Vasudeva | B23B 51/0426 408/204 |
| 2010/0286694 | A1 * | 11/2010 | Rio | A61B 17/1631 606/80 |
| 2011/0036212 | A1 * | 2/2011 | Santamarina | B25B 23/14 81/436 |
| 2013/0243541 | A1 * | 9/2013 | Stagge | B23C 5/26 279/96 |
| 2014/0207141 | A1 * | 7/2014 | Kehres | A61B 17/1778 606/80 |
| 2014/0343454 | A1 * | 11/2014 | Miller | A61B 10/025 600/567 |
| 2016/0000449 | A1 * | 1/2016 | Aman | A61B 17/1622 173/217 |
| 2016/0278802 | A1 * | 9/2016 | Cihak | B23B 31/005 |
| 2016/0361069 | A1 * | 12/2016 | Ardel | A61B 17/1626 |
| 2017/0100822 | A1 * | 4/2017 | Cutler | F16D 7/044 |
| 2019/0223930 | A1 | 7/2019 | Nolan et al. | |
| 2019/0388115 | A1 * | 12/2019 | Nguyen | A61B 17/162 |
| 2020/0008787 | A1 * | 1/2020 | Koltz | A61B 17/7074 |
| 2022/0192681 | A1 * | 6/2022 | Hilton | B23B 31/008 |
| 2024/0423642 | A1 * | 12/2024 | Hilton | A61B 17/162 |

OTHER PUBLICATIONS

European Search Report for Application No. 21214377.0-1122, mailed May 13, 2022 (9 pages).

* cited by examiner

ROTARY CUTTING TOOL AND POWERED HANDPIECE ADAPTOR ASSEMBLIES, SYSTEMS, AND METHODS OF USE

CROSS-REFERENCE TO RELATED APPLICATIONS

This application is a divisional of U.S. patent application Ser. No. 17/523,335 filed Nov. 10, 2021, which claims priority to U.S. Provisional Patent Application No. 63/127,533 filed Dec. 18, 2020. The entire disclosures of the above applications are incorporated herein by reference.

FIELD

The present disclosure relates to rotary-type surgical cutting tools and powered handpieces (or drills). More particularly, it relates to interface devices for connecting a rotary-type surgical cutting tool with a powered handpiece.

BACKGROUND

Powered surgical handpieces (also referred to as drills) are commonly used in many medical specialties to drive surgical tools. For example, powered surgical handpieces are used to drive surgical drills, blades or other cutting tools in performing various diverse cutting-type functions including drilling, tapping, resection, dissection, debridement, shaving, pulverizing, and shaping of anatomical tissue including bone. The handpieces are typically configured for selective coupling to, and driving of, a variety of different rotary-type surgical cutting tools that are each designed to perform a specific procedure. During use, based upon the specific surgical procedure, the surgeon selects the appropriate surgical tool and mounts it to the powered handpiece. The powered handpiece is then operated to move (e.g., rotation, oscillation) the tool in performing the surgical procedure. Additional procedural steps can later be performed by mounting a differently-styled tool to the same powered handpiece.

The improved capabilities of powered surgical handpieces, as well as the vast number of surgical cutting tools now available, have undoubtedly greatly increased the number of neurological, spine, ENT/head/neck and other procedures that a surgeon can perform utilizing a single surgical system (i.e., a single powered handpiece with multiple surgical cutting tools). Selective driven coupling between the powered handpiece and each tool is typically effectuated within a housing of the handpiece. The housing carries an internal drive chuck configured to receive a tang or shank of the surgical cutting tool in a mating fashion. Thus, the tang of each surgical cutting tool useful with a particular handpiece has a common shape, with this shape corresponding to the handpiece drive chuck (e.g., circular, hexagonal). The drive chuck is connected to (or formed as part of) a drive shaft; upon coupling of the surgical cutting tool to the drive chuck, powered rotation of the drive shaft rotates the cutting tool.

Conventionally, the cutting tool, including the tang, is generally shaped as an elongated cylinder defining a single central axis about which the tool is driven and rotated during use. The handpiece drive chuck forms a corresponding, generally cylindrical-shaped passage for receiving the tang, effectuating a coupled connection and subsequent driven interface at point contacts created solely about the single central axis. The tang (or other regions of the cutting tool) may include recesses, grooves, or other features deviating from a truly cylindrical shape for purposes of effectuating an axial and/or rotational lock relative to the drive chuck. Where the coupling features of the drive chuck and the tang of a particular surgical tool do not afford a true match (e.g., due to wear at the drive chuck), coupling between the surgical tool and the powered handpiece may be less than robust.

SUMMARY

The inventors of the present disclosure have recognized a need to address one or more of the above-mentioned problems. The details of one or more aspects of the disclosure are set forth in the accompanying drawings and the description below. Other features, objects, and advantages of the techniques described in this disclosure will be apparent from the description and drawings, and from the claims.

Some aspects of the present disclosure relate to an adaptor assembly for coupling a surgical cutting tool to a drive chuck of a powered handpiece such that driven rotation of the drive chuck is transferred to the surgical cutting tool by the adaptor assembly. The adaptor assembly includes a rod, a collet and an enclosure. The rod defines a proximal region opposite a distal region. The proximal region provides an adaptor male coupling portion configured to engage a drill drive chuck. The collet defines a trailing region opposite a leading region. The leading region provides an adaptor female coupling portion configured to engage a surgical cutting tool tang. The distal region of the rod and the trailing region of the collet form complementary engagement features for coupling the rod to the collet. Further, a format of the adaptor male coupling portion of the rod differs from a format of the adaptor female coupling portion of the collet such that the adaptor male coupling portion is incompatible with the adaptor female coupling portion. The enclosure rotatably maintains the collet. Upon final assembly of the rod to the collet, driven rotation of the rod is transferred to the collet. During use, the adaptor assembly can facilitate coupling of a surgical cutting tool to a powered handpiece under circumstances where the coupling feature(s) provided with the cutting tool are incompatible with those of the powered handpiece. The adaptor assembly is coupled to the powered handpiece, including establishing a robust connection between the rod and the drive chuck at an interface of the drill female coupling portion and the adaptor male coupling portion. That is to say, a format of the adaptor male coupling portion provided with the adaptor assembly is compatible with a format of the drill female coupling portion provided with the drill chuck. The surgical cutting tool is coupled to the adaptor assembly, including establishing a robust connection between a surgical cutting tool tang and the collet at an interface of the tool male coupling portion and the adaptor female coupling portion. That is to say, a format of the adaptor female coupling portion provided with the adaptor assembly is compatible with a format of the tool male coupling portion provided with the surgical cutting tool.

Other aspects of the present disclosure relate to a conversion device for coupling a drive device, including a collet for receiving a surgical cutting tool, to a drive chuck of a powered handpiece such that driven rotation of the drive chuck is transferred to the collet by the conversion device. The conversion device includes a rod and a cover. The rod defines a proximal region opposite a distal region. The proximal region provides an adaptor male coupling portion configured to engage a drill drive chuck. The distal region provides a conversion coupling portion configured to engage a collet of a drive device. The cover rotatably maintains the rod, and defines a first end section opposite a second end section. The first end section is configured for selective attachment to a powered handpiece. The second end section is configured for selective attachment to a drive device.

Other aspects of the present disclosure relate to a drive device for coupling a surgical cutting tool to a conversion device assembled to a drive chuck of a powered handpiece such that driven rotation of a rod of the conversion device by the drive chuck is transferred to the surgical cutting tool by the drive device. The drive device includes a collet and an enclosure. The collet defines a trailing region opposite a leading region. The trailing region provides a drive coupling portion configured to engage a rod of a conversion device. The leading region provides an adaptor female coupling portion configured to selectively engage a surgical cutting tool tang. The enclosure rotatably maintains the collet, and defines a proximal end region. The proximal end region is configured for selective attachment to a conversion device.

Other aspects of the present disclosure relate to a surgical system for cutting tissue. The surgical system includes a powered handpiece, a surgical cutting tool, and an adaptor assembly. The powered handpiece includes a housing and a drive chuck. The drive chuck is rotatably maintained by the housing and provides a drill female coupling portion. The surgical cutting tool includes a shaft, cutting head, and tang. The shaft defines opposing, first and second ends. The cutting head is provided adjacent the first end. The tang is provided adjacent the second end and provides a tool male coupling portion. The adaptor assembly includes a rod, a collet, and an enclosure. The rod defines a proximal region opposite a distal region. The proximal region provides an adaptor male coupling portion configured to engage the drill female coupling portion. The collet defines a trailing region opposite a leading region. The leading region provides an adaptor female coupling portion configured to engage the tool male coupling portion. The distal region of the rod and the trailing region of the collet form complementary engagement features for coupling the rod to the collet. The enclosure rotatably maintains the collet. A format of the tool male coupling portion differs from a format of the drill female coupling portion such that the tool male coupling portion is incompatible with the drill female coupling portion. Upon final assembly of the rod to the collet, driven rotation of the drive chuck is transferred to the surgical cutting tool by the adaptor assembly.

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

Figure 1:
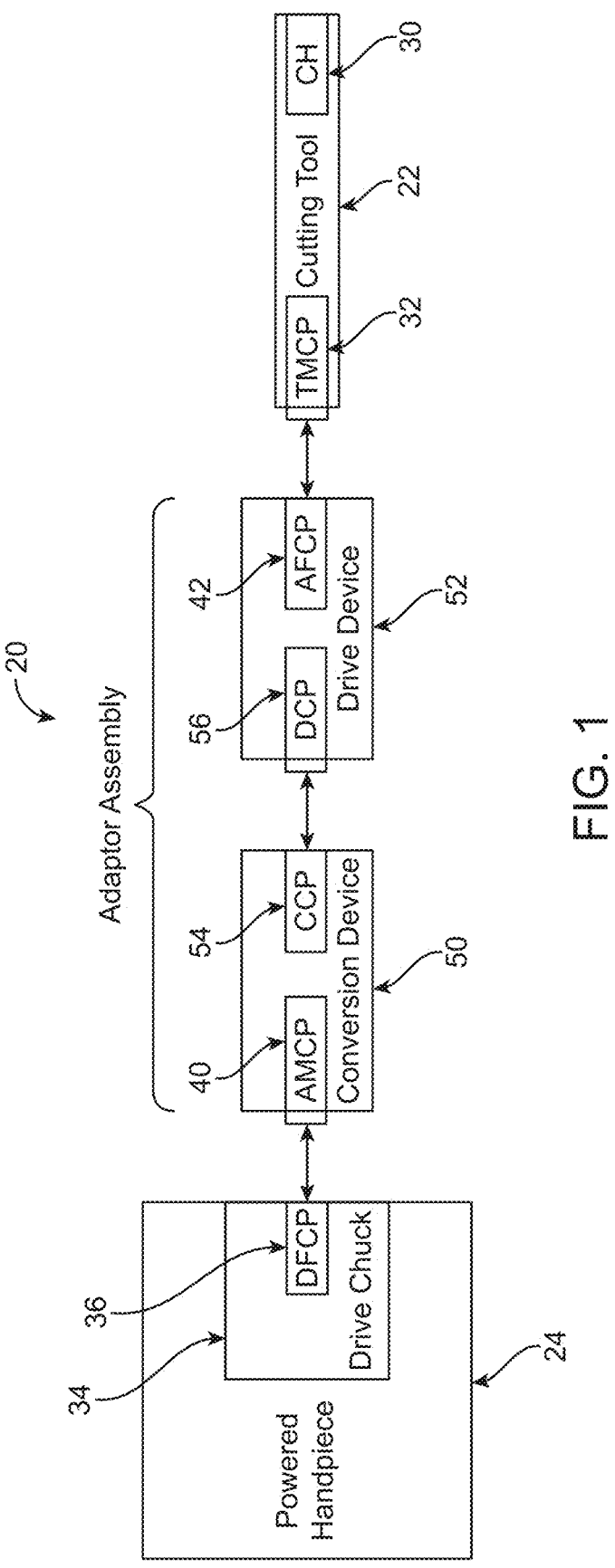
FIG. 1 schematically illustrates an adaptor assembly as part of a surgical system in accordance with principles of the present disclosure.

With reference to FIG. 1, some embodiments of the present disclosure provide an adaptor assembly 20 for coupling a surgical cutting tool 22 to a powered handpiece or drill 24 such that the drill 24 operates to drive rotation of the cutting tool 22. The adaptor assemblies 20 of the present disclosure can assume various forms, and in some embodiments facilitate indirect coupling between dissimilar coupling features provided with the surgical cutting tool 22 and the powered handpiece 24. As a point of reference and as described in greater detail below, the cutting tool 22 can assume various forms, and generally includes or defines a cutting head 30 opposite a tool male coupling portion (TMCP) 32. The powered handpiece 24 can also assume various forms, and generally includes a drive chuck 34 forming or providing a drill female coupling portion (DFCP) 36. With this in mind, the adaptor assembly 20 includes or provides an adaptor male coupling portion 40 and an adaptor female coupling portion 42. The adaptor male coupling portion 40 is formatted in accordance with the drill female coupling portion 36; the drill female coupling portion 36 and the adaptor male coupling portion 40 have complementary engagement features. The adaptor female coupling portion 42 is formatted in accordance with the tool male coupling portion 32; the adaptor female coupling portion 42 and the tool male coupling portion 32 have complementary engagement features. While the complementary engagement features provided by the various coupling portions can assume various forms, in some embodiments, a format of the tool male coupling portion 32 is incompatible with a format of the drill female coupling portion 36. That is to say, were an attempt made to insert the cutting tool 22 into the drive chuck 34, the tool male coupling portion 32 would not mate with the drill female coupling portion 36 in a manner affording a robust coupling appropriate for safe use as part of a surgical procedure in which the surgical cutting tool 22 is intended to be rotated by the powered handpiece 24 for cutting tissue. Commensurate with these explanations, then, in some embodiments a format of the adaptor male coupling portion 40 differs from, and is incompatible with, a format of the adaptor female coupling portion 42;

In some embodiments, the adaptor assemblies 20 can include two or more separable components, such as a conversion device 50 and a drive device 52. The conversion device 50 forms or carries the adaptor male coupling portion 40, and the drive device 52 forms or carries the adaptor female coupling portion 42. The conversion device 50 and the drive device 52 can be configured for selective attachment to one another, for example by providing a conversion coupling portion (CCP) 54 with the conversion device 50 and a complementary drive coupling portion (DCP) 56 with the drive device 50. The conversion coupling portion 54 and the drive coupling portion 56 are formatted to incorporate complementary engagement features (e.g., the conversion coupling portion 54 can be formatted to have a male-type construction and the drive coupling portion 56 as a female-type construction, or vice-versa).

During use, the conversion device 50 can be selectively assembled to the powered handpiece 24, including a robust engaged interface between the drill female coupling portion 36 and the adaptor male coupling portion 40. The conversion device 50 can be selectively or permanently assembled to the drive device 52, including a robust engaged interface between the conversion coupling portion 54 and the drive coupling portion 56. Finally, the cutting tool 22 can be selectively assembled to the drive device 52, including a robust engaged interface between the adaptor female coupling portion 42 and the tool male coupling portion 32. In this assembled state, driven rotation (e.g., rotate in a single direction or oscillate) of the drive chuck 34 is transferred to the cutting tool 22 via the adaptor assembly 20. While FIG. 1 reflects the conversion device 50 and the drive device 52 as being separable from one another, in other embodiments a more permanently connection can be established. For example, and as shown in FIG. 2, another embodiment adaptor assembly 20' of the present disclosure has an integral or homogenous construction, and includes the adaptor male coupling portion 40 and the adaptor female coupling portion 42 as described above.

Figure 2:
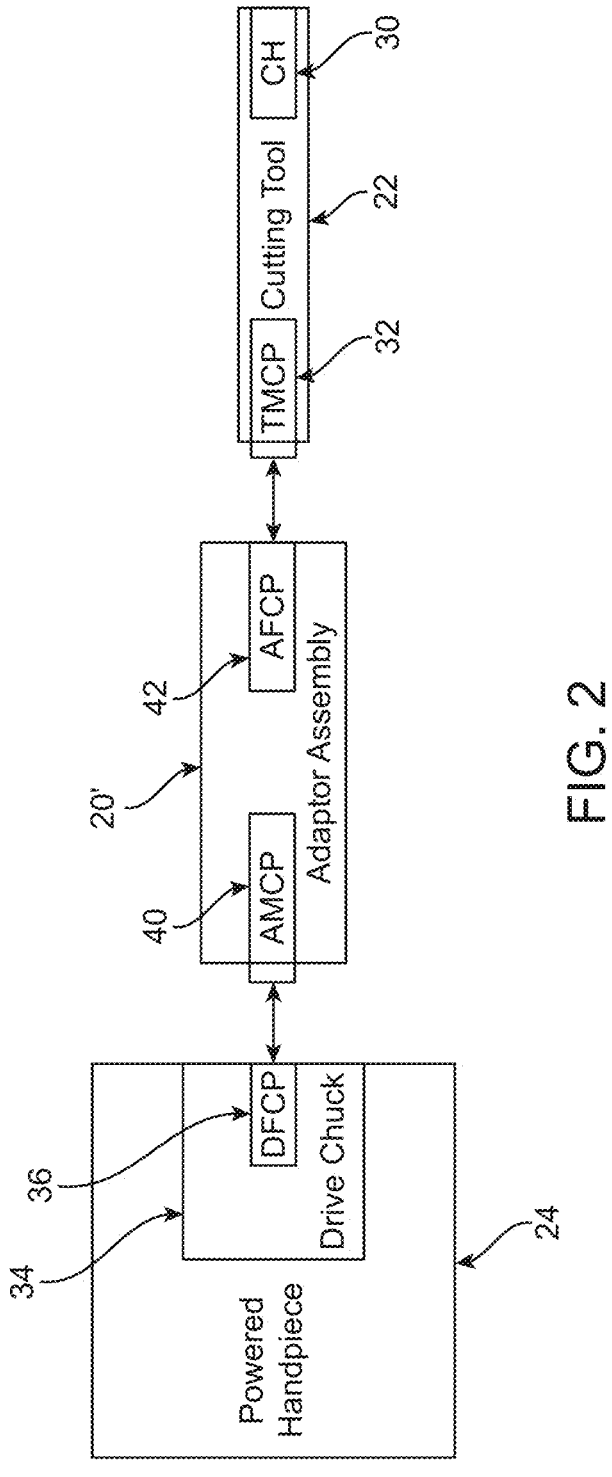
FIG. 2 schematically illustrates another adaptor assembly as part of a surgical system in accordance with principles of the present disclosure.

With reference to FIGS. 1 and 2, some aspects of the present disclosure relate to the conversion device 50 alone, to the drive device 52 alone, or to the adaptor assembly 20, 20' (that may or may include separable conversion and drive devices). Yet other aspects of the present disclosure relate to surgical cutting system including the powered handpiece 24, the adaptor assembly 20, 20', and the surgical cutting tool 22.

Figure 3:
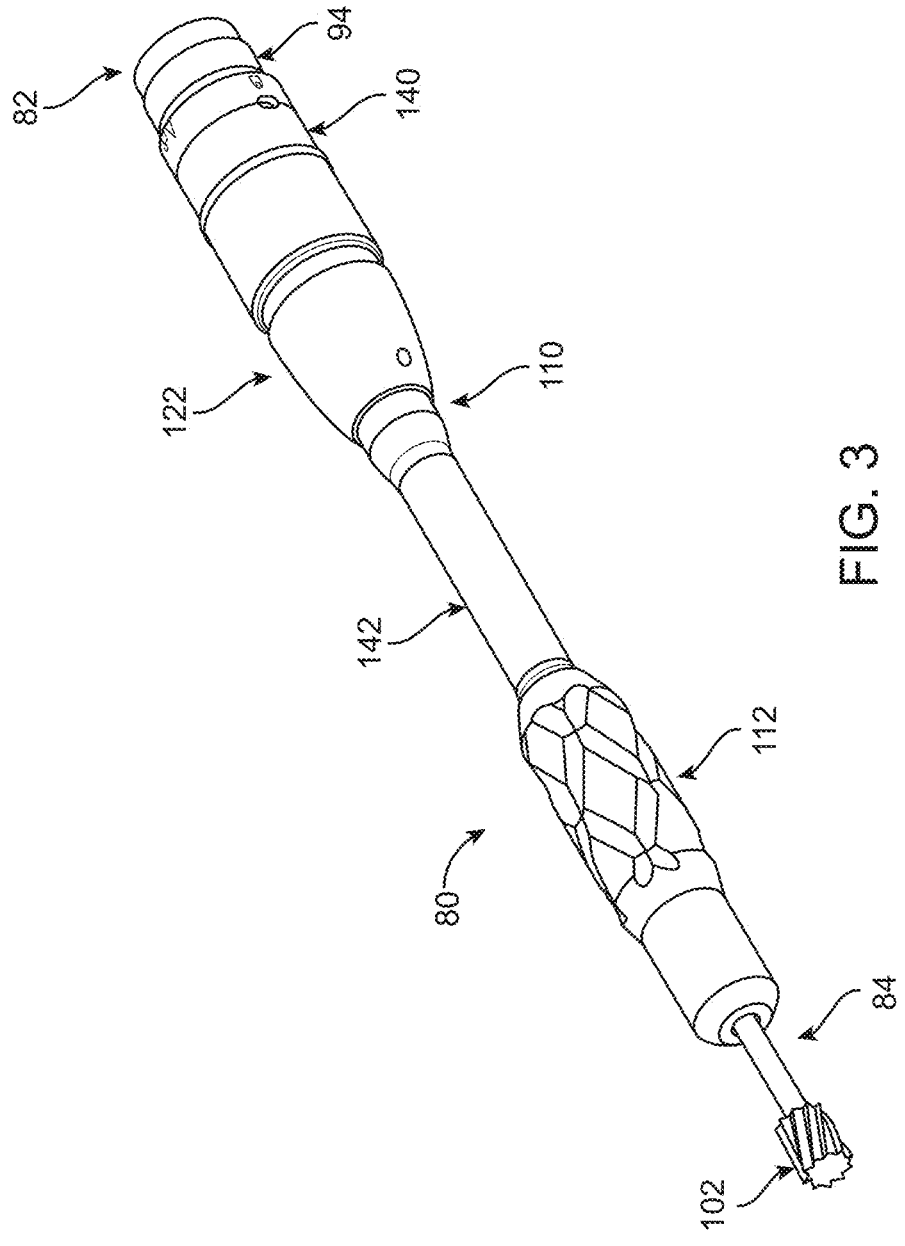
FIG. 3 is a perspective view of a surgical system including an adaptor assembly in accordance with principles of the present disclosure.
Figure 4:
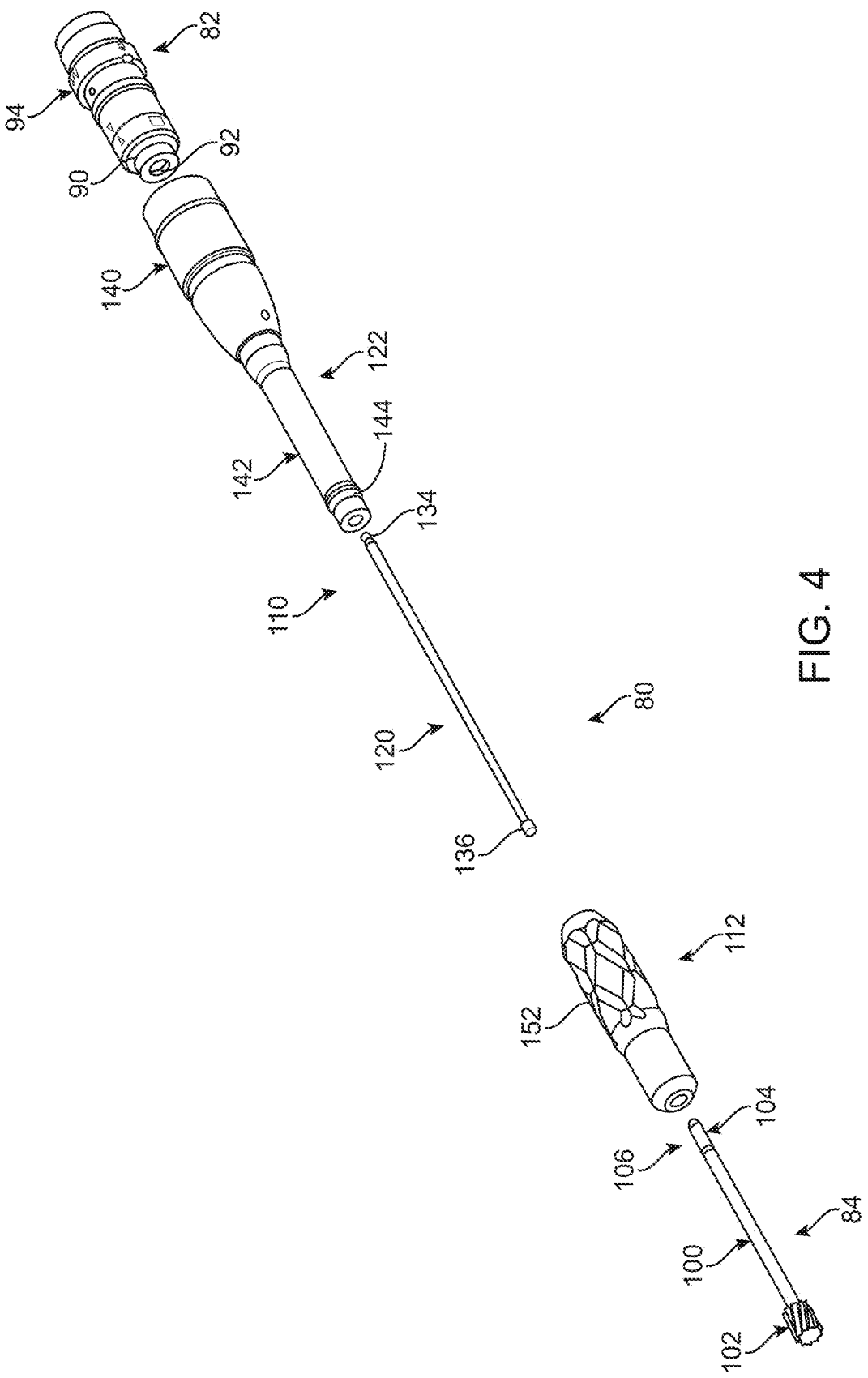
FIG. 4 is an exploded perspective view of the surgical system of FIG. 3.

FIGS. 3 and 4 illustrate one example of an adaptor assembly 80 of the present disclosure as part of surgical system that also includes a powered handpiece 82 and a surgical cutting tool 84. The powered handpiece 82 and the cutting tool 84 can each assume a wide variety of forms as will be apparent to one of ordinary skill. For example, while only a portion of the powered handpiece 82 is shown, commensurate with the above explanations, the powered headpiece 82 generally includes a drive chuck 90 forming or carrying a drill female coupling portion 92. The drive chuck 90 is carried by or rotatable relative to a drill housing 94. Further, the cutting tool 84 generally includes a shaft 100 forming or carrying a cutting head 102 opposite a tang 104 that otherwise forms or carries a tool male coupling portion 106. With this in mind, the adaptor assembly 80 includes a conversion device 110 and a drive device 112. Details on the various components are provided below. In general terms, the conversion device 110 is configured for selective attachment to the powered handpiece 82, including engagement with the drill female coupling portion 92. The drive device 112 is attachable (either releasable attachment or permanently attached) to the conversion device 110, and is configured for selective attachment to the cutting tool 84, including engagement with the tool male coupling portion 106. Upon final assembly, driven rotation (e.g., rotate in a single direction or oscillate) of the drive chuck 90 is transferred to the cutting tool 84 via the adaptor assembly 80.

Figure 5:
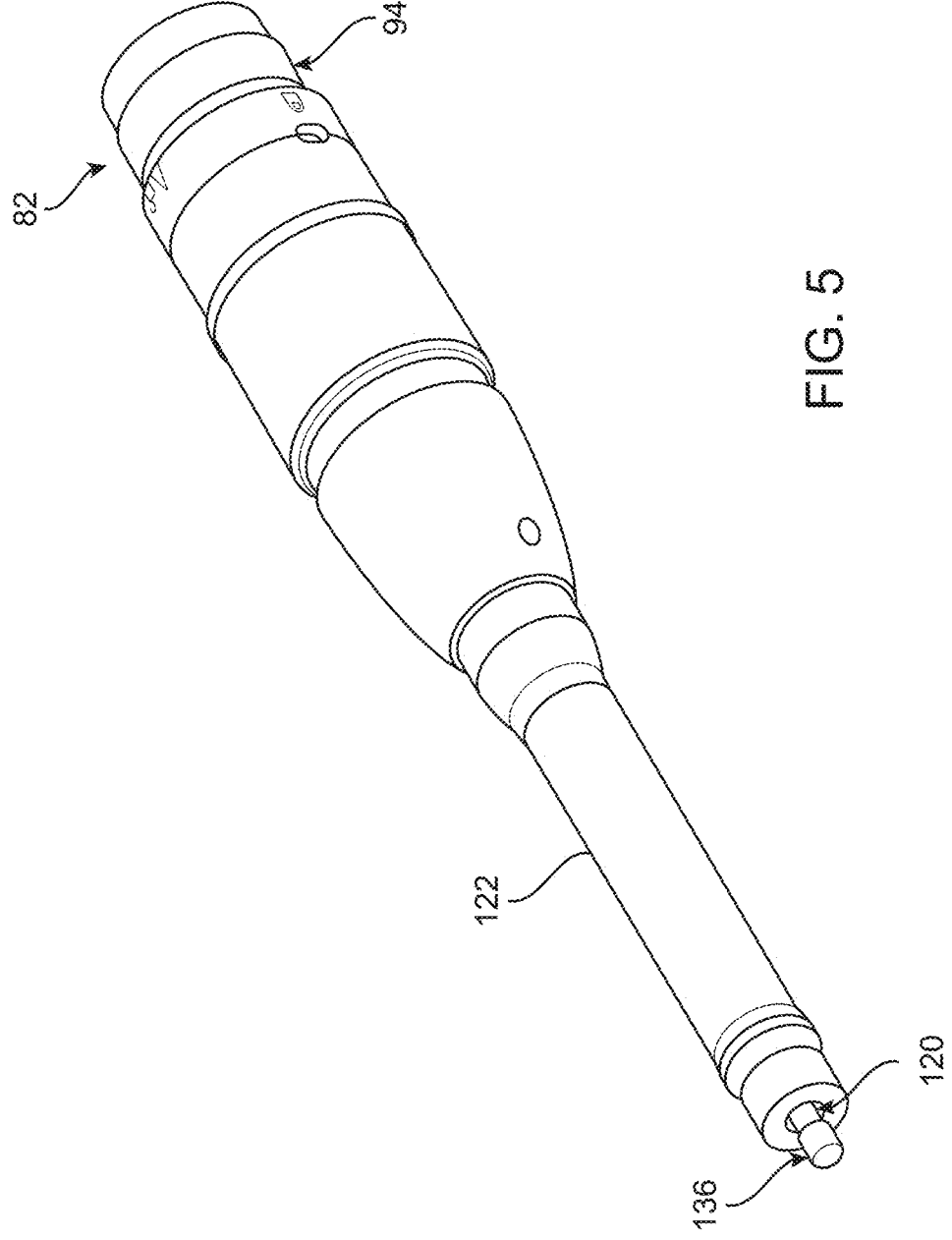
FIG. 5 is a perspective view of a portion of the surgical system of FIG. 3, including a conversion device of the adaptor assembly mounted to a powered handpiece.

The conversion device 110 includes a rod 120 and a cover 122. The rod 120 is rotatably maintained within the cover 122, and defines a proximal region opposite a distal region. The proximal region forms or carries an adaptor male coupling portion 134 configured to engage the drill female coupling portion 92. The distal region forms or carries a conversion coupling portion 136 configured to engage a component of the adaptor device 112. Non-limiting examples of possible coupling portion formats envisioned by the present disclosure are provided below. The cover 122 can assume various shapes and sizes appropriate for rotatably maintaining the rod 120 (e.g., ball bearing assemblies can be disposed within the cover 122 and mounted over the rod 120). In some embodiments, the cover 122 forms or defines a first end section 140 opposite a second end section 142. The end sections 140, 142 can be integrally formed, or can be separately manufactured and subsequently assembled to one another. Regardless, in some embodiments, the first end section 140 includes or incorporates features appropriate for selective attachment to the drill housing 94. For example, the first end section 140 can be configured to engage the drill housing 94 in an interference fit. Other attachment formats are also acceptable as a function of the drill housing 94 construction as are known in the art (e.g., the first end section 140 can form internal threads for threadably engaging external threads on the drill housing 94; a ball-and-detent format can be employed, etc.). The second end section 142 includes or incorporates features configured for selective attachment with corresponding feature(s) of the driver device 112 as described below. By way of non-limiting example, the second end section 142 can form or carry exterior threads 144. Regardless, in some embodiments and with additional reference to FIG. 5, an axial length of the rod 120 relative to an axial length of the cover 122 is selected such that upon final assembly of the cover 122 to the drill housing 94 (including engagement between the adaptor male coupling portion 134 with the drill female coupling portion 92), the conversion coupling portion 136 projects beyond the cover 122 for reasons made clear below.

Figure 6:
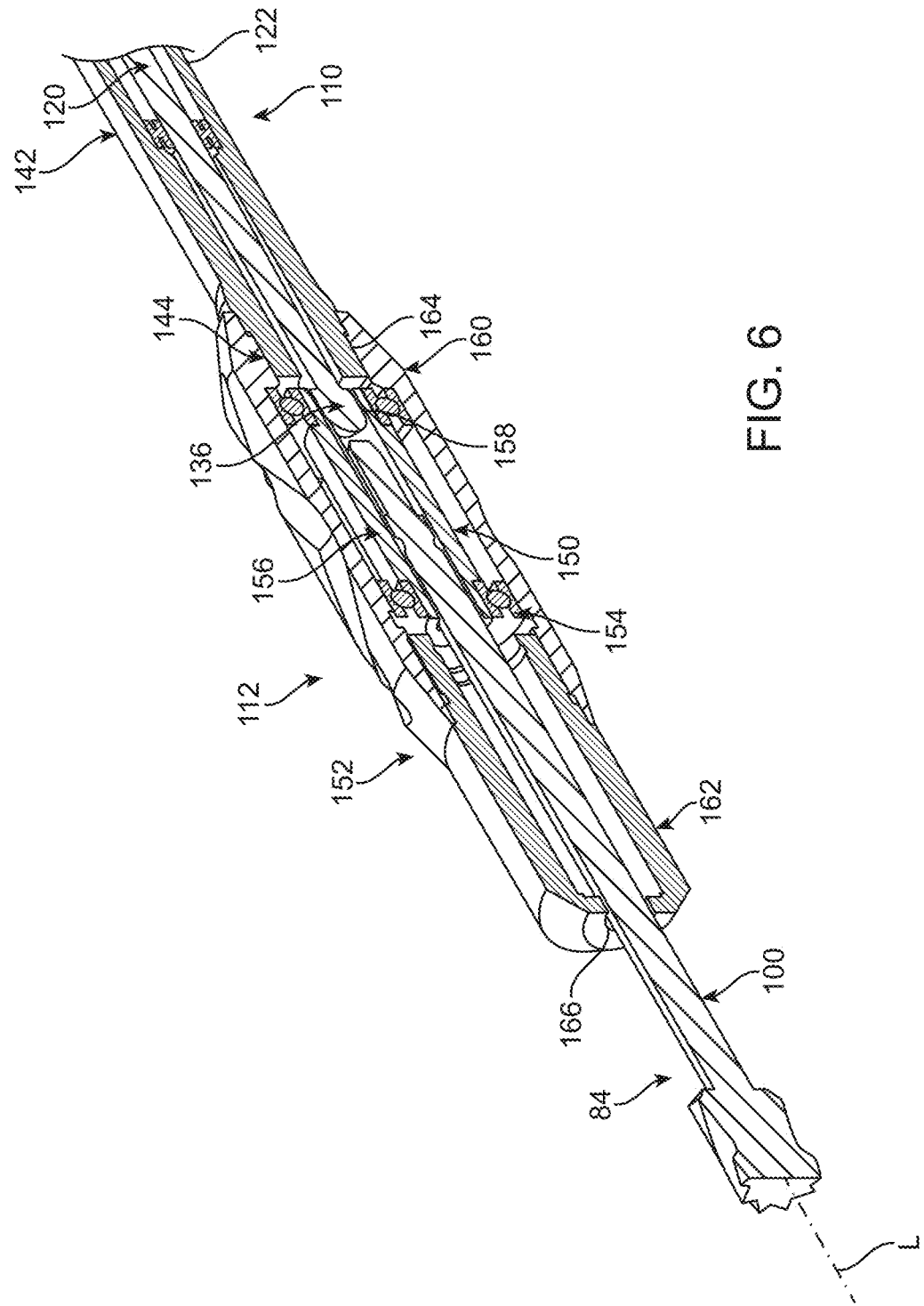
FIG. 6 is a perspective, cross-sectional view of a portion of the surgical system of FIG. 3, including a drive device of the adaptor assembly mounted to the conversion device along with a surgical cutting tool.

Returning to FIGS. 3 and 4, and with additional reference to FIG. 6 (that otherwise depicts the drive device 112 assembled to the conversion device 110, and the cutting tool 84 assembled to the drive device 112), the drive device 112 can include a collet 150 and an enclosure 152. The collet 150 is rotatably maintained within the enclosure 152 (e.g., by one or more bearing assemblies 154). Further, the drive device 112 forms or carries an adaptor female coupling portion 156 (referenced generally) for selectively engaging the tool male coupling portion 106, and a drive coupling portion 158 (referenced generally) for selectively engaging the conversion coupling portion 136 of the conversion device 110 as described in greater detail below.

The enclosure 152 can assume various shapes and sizes appropriate for rotatably maintaining the collet 150 and for selectively receiving the cutting tool 84. In some embodiments, the enclosure 152 forms or defines a proximal end region 160 opposite a distal end region 162. The end regions 160, 162 can be integrally formed, or can be separately manufactured and subsequently assembled to one another. Regardless, in some embodiments, the proximal end region 160 includes or incorporates features appropriate for selective attachment to the conversion device cover 122. For example, and as described above, in some non-limiting examples, the second end section 142 of the conversion device cover 122 can form or carry the exterior threads 144. With these and similar embodiments, the proximal end region 160 can form or carry corresponding interior threads 164, facilitating threaded engagement between the cover 122 and the enclosure 152. Other attachment formats (e.g., interference fit, ball-and-detent, etc.) are also acceptable. The distal end region 162 can form or carry features that facilitate rotationally supporting the shaft 100 of the cutting tool 84. For example, a size or diameter of an entry bore 166 to an interior of the enclosure 152 can approximate (e.g., be slightly larger than) an expected diameter of the cutting tool shaft 100. In addition or alternatively, one or more rotational support assemblies (e.g., ball bearing assemblies) can be carried by the distal end region 162.

The complementary format of the conversion coupling portion 136 and the drive coupling portion 158 can assume various forms conducive to a robust engagement therebetween whereby driven rotation of the rod 120 is transferred to the collet 150 (i.e., upon engagement between the conversion coupling portion 136 and the drive coupling portion 158, the collet 150 rotates with rotation of the rod 120). In some embodiments, the conversion coupling portion 136 and the drive coupling portion 158 are configured for assembly/disassembly in an axial manner. For example, relative to a longitudinal axis L defined by the collet 150, the conversion coupling portion 136 engages the drive coupling portion 158 by directing the collet 150 axially toward the rod 120 (and/or vice-versa) in a direction of the longitudinal axis L. With these and related embodiments, a location of the drive coupling portion 158 relative to a longitudinal length of the enclosure 152 has a pre-determined relationship to the known or pre-determined longitudinal location of the conversion coupling portion 136 relative to the cover 122 (with embodiments in which the conversion coupling portion 136 is located outside of or beyond the cover 122); in particular, the drive coupling portion 158 is positioned such that with assembly of the enclosure 152 to the cover 122, the drive coupling portion 158 is longitudinally aligned with the conversion coupling portion 136. The conversion coupling portion 136 can be removed from engagement with the drive coupling portion 158 by directing the collet 150 axially away from the rod 120 (and/or vice-versa) in a direction of the longitudinal axis L. With these and related embodiments, the conversion coupling portion 136 and the drive coupling portion 158 can have a complementary male/female-type format. With the non-limiting example of FIG. 6, the conversion coupling portion 136 has a male-type configuration, sized and shaped to be received within a female-type configuration of the drive coupling portion 158. In other embodiments, the conversion coupling portion 136 can have a female-type construction and the drive coupling portion 158 can have a complementary male-type construction.

Figure 7:
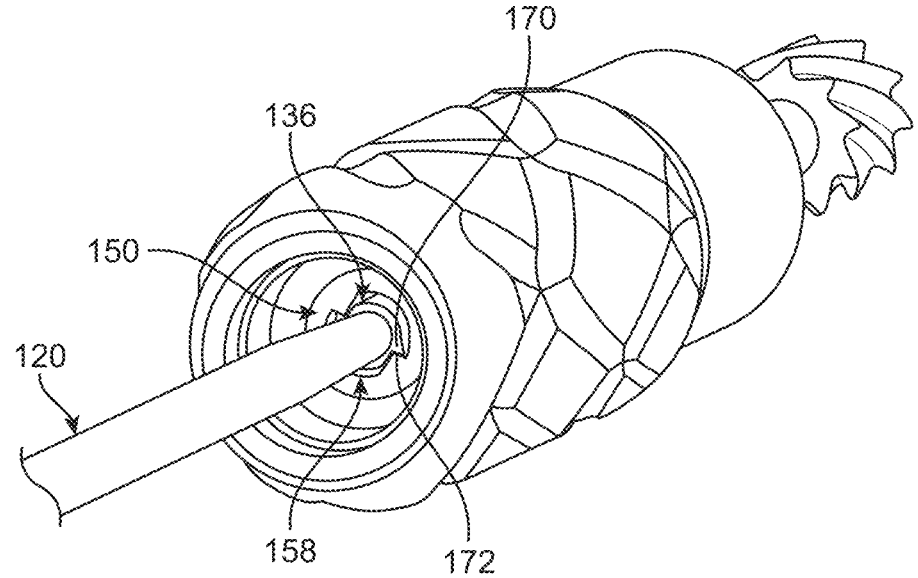
FIG. 7 is a perspective view of a portion of the surgical system of FIG. 3, including a portion of the conversion device mounted to the drive device.

FIG. 7 illustrates one non-limiting example of a construction of the conversion coupling portion 136 (referenced generally) and the drive coupling portion 158 (referenced generally) in an engaged state. The conversion coupling portion 136 provided with or by the rod 120 has a male-type format, forming or defining one or more drive surfaces 170 (one of which is identified in FIG. 7). The drive coupling portion 158 provided with or by the collet 150 has a female-type format, forming or defining one or more driven surfaces 172 (one of which is identified in FIG. 7). Upon insertion of the conversion coupling portion 136 into the drive coupling portion 158, the drive surface(s) 170 slidingly contact or abut a corresponding one of the driven surface(s) 172. In this engaged state, with rotation or torque at the rod 120 is transferred to the collet 150 at the drive surface 170/driven surface 172 interface. It will be understood by one of skill in the art that other complementary coupling formats can be employed for the conversion coupling portion 136 and the drive coupling portion 158 that may or may not be implicated by the features of FIG. 7.

Figure 8:
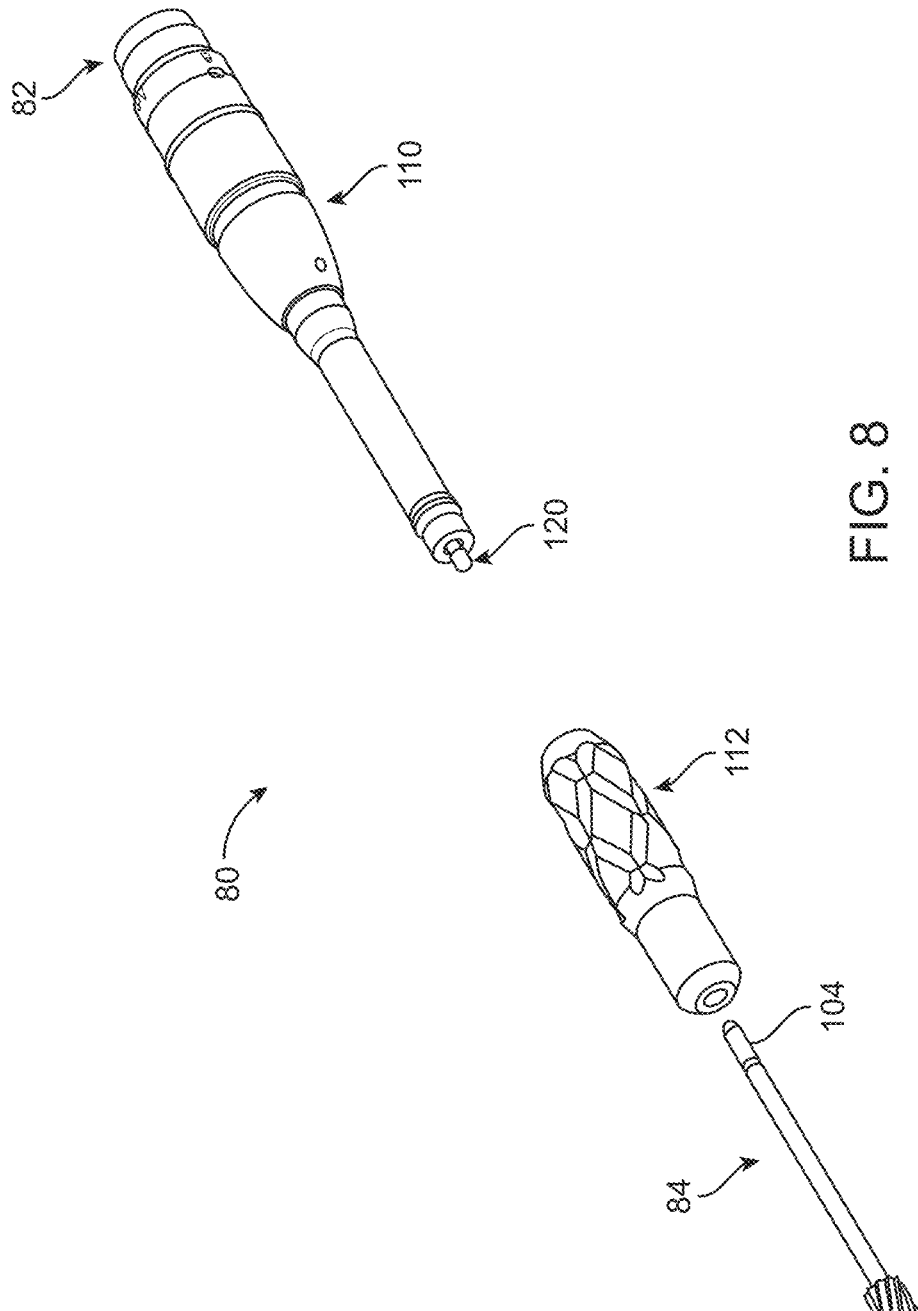
FIG. 8 is a perspective view of the surgical system of FIG. 3, illustrating an intermediate stage of assembly in which a conversion device of the adaptor assembly is mounted to the powered handpiece.

During use, the conversion device 110 is assembled to the powered handpiece 82 as shown in FIG. 8. In some embodiments, the conversion device 110 can be permanently attached to the powered handpiece 82. Regardless, the rod 120 is coupled to the drive chuck 90 (FIG. 4). The drive device 112 is assembled to the conversion device 110, for example as described above and shown in FIG. 7, thereby completing the adaptor assembly 80. Finally, the surgical cutting tool 84 is mounted to the adaptor assembly 80 (e.g., at the drive device 112), including the tang 104 coupling with the collet 150 (FIG. 6). Final assembly of the surgical system is represented by FIG. 3. The powered handpiece 82 can be operated as desired to rotate the cutting tool 84 via the adaptor assembly 80 in performing a surgical procedure.

With reference to FIG. 4, a format of the adaptor male coupling portion 134 can be selected in accordance with any known, or in the future developed, drill female coupling portion 92. In this regard, the powered handpiece 82 can assume any form appropriate for use with driving a rotary-type surgical cutting tool, for example a powered handpiece or drill available from Medtronic, Inc. under the trade name Midas Rex™, such as the Midas Rex™ Legend™ surgical drill, the Midas Rex™ MR7™ surgical drill, the Midas Rex™ MR8™ surgical drill, etc. The powered handpieces of the present disclosure can employ various drive assemblies or motors (e.g., pneumatically powered or driven, electrically powered or driven, etc.) as known in the art for effectuating driven rotation at desired speeds, and generally include the housing 94 maintaining a drive shaft that mechanically couples or links a motor (not shown) to the drive chuck 90 (e.g., akin to a collet) via a coupling assembly as is known in the art. The drive chuck 90, in turn, forms or provides the drill female coupling portion 92. The drill female coupling portion 92 can assume a wide variety of forms or formats, and the present disclosure is in no way limited to a particular coupling configuration at the powered handpiece 82. In more general terms, the drill female coupling portion 92 is configured to selectively receiving/load an inserted component in a manner facilitating driven rotation of the loaded component.

Figure 9:
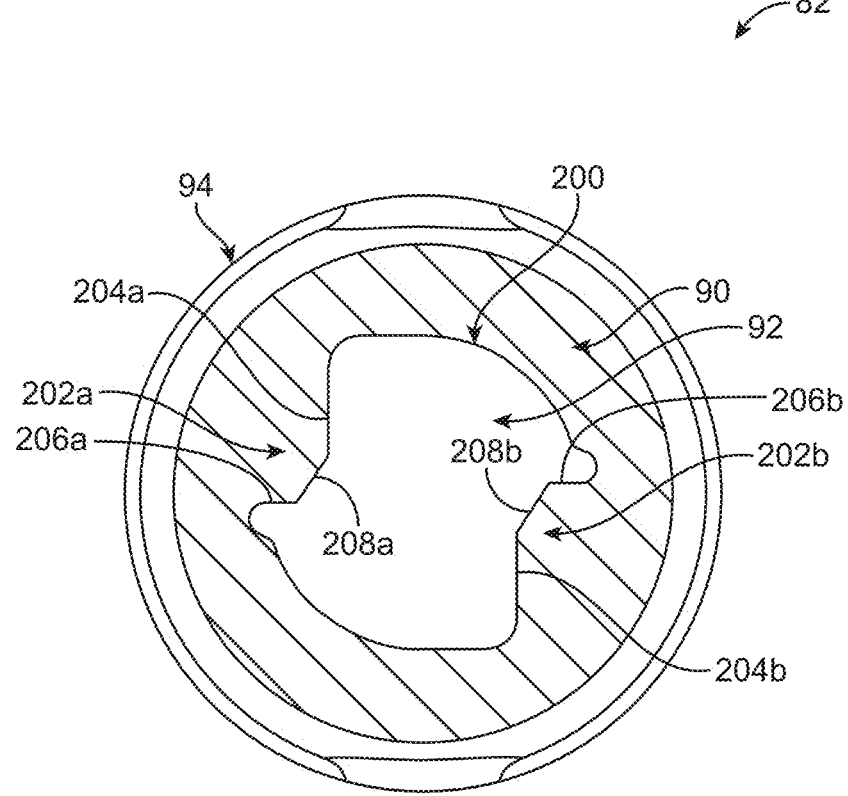
FIG. 9 is a simplified cross-sectional view of a portion of a powered handpiece useful with the adaptor assemblies of the present disclosure and illustrating an example drill chuck having a drill female coupling portion.

By way of non-limiting example, FIG. 9 is a simplified representation of a portion of the powered handpiece 82, illustrating but one possible example of the drill female coupling portion 92 (referenced generally). In the view of FIG. 9, the powered handpiece 82 includes the housing 94 and the drive chuck 90. The drive chuck 90 can have an elongated tubular or hub-like construction, and defines an interior passage sized to receive an appropriately-formatted, inserted component. In some embodiments, a perimeter shape of the interior passage serves as the drill female coupling portion 92. For example, a maximum diameter of the interior passage id defined by a guide face 200. An interior geometry of the drive chuck 90 defines opposed drive pins or drive bodies 202a, 202b that otherwise represent radially inward projections from the guide face 200. The first drive pin 202a defines a first drive surface 204a and a second drive surface 206a. The drive surfaces 204a, 206a do not directly intersect at a singular corner; instead, a recessed surface 208a extends between the drive surfaces 204a, 206a. The second drive pin 202b similarly defines a first drive surface 204b, a second drive surface 206b, and a recessed surface 208b. The drive pins 202a, 202b have a symmetrical yet offset arrangement.

Figure 10:
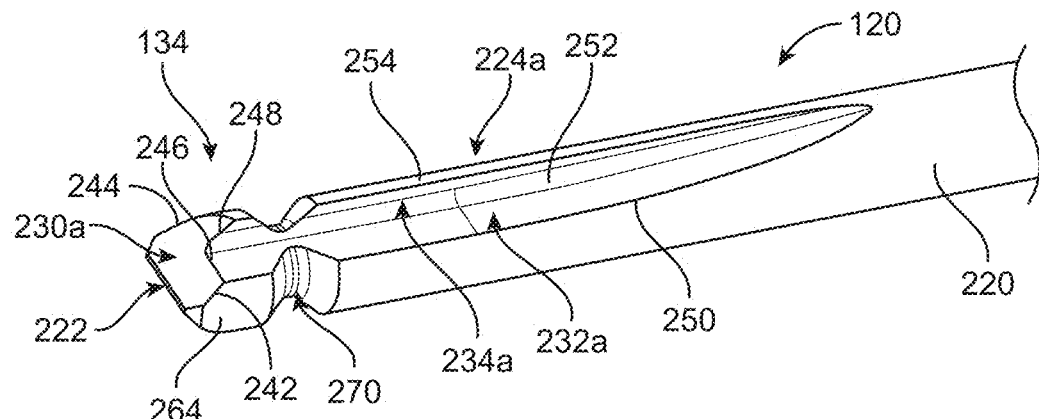
FIG. 10 is a perspective view of a rod component useful with the adaptor assemblies of the present disclosure and illustrating an example adaptor male coupling portion.
Figure 11:
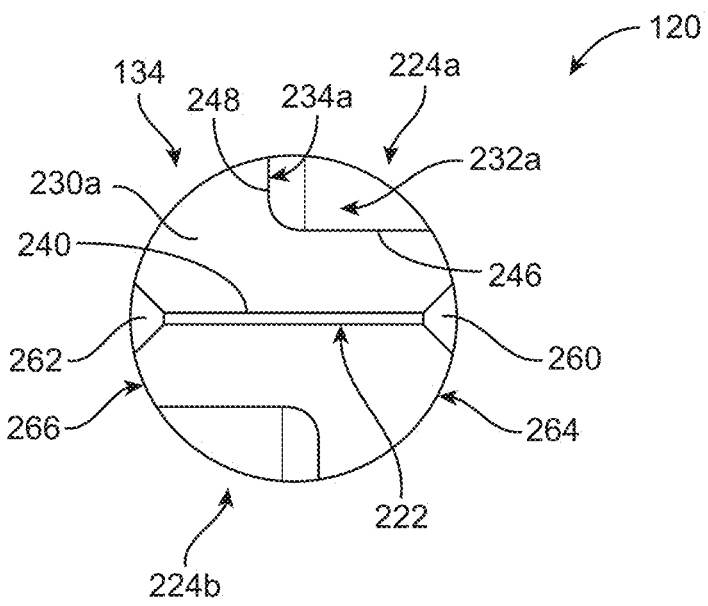
FIG. 11 is an end view of the rod of FIG. 10.

The adaptor male coupling portion 134 (FIG. 4) can be formatted in accordance with the drill female coupling portion 92 of FIG. 9. For example, a portion of one non-limiting example of the rod 120 is shown in FIGS. 10 and 11, illustrating a possible format of the adaptor male coupling portion 134. The adaptor male coupling portion 134 extends from a stem portion 220 to a proximal end 222. The adaptor male coupling portion 134 includes a first interface structure 224a and a second interface structure 224b. The interface structures 224a, 224b can be identical (or embodying a mirror image thereof) in some embodiments (e.g., symmetrically off-set), and can be formed or cut into an optional right cylinder initial shape of the rod 120.

The first interface structure 224a can include or define a deflection surface 230a, a first driven surface 232a, and a second driven surface 234a. The second interface structure 224b can have an identical construction. The deflection surface 230a is bound by a leading edge 240, first and second side edges 242, 244, and first and second intermediate or interposing connecting lateral edges 246, 248. A face of the deflection surface 230a can be substantially planar (i.e., within 5% of a truly planar or flat surface) in some non-limiting embodiments. In some embodiments, surface features can optionally be incorporated into the deflection surface 230a such that an entirety of the deflection surface 230a need not necessarily have a constant or uniform shape. However, a major plane defined by the deflection surface 230a is oriented oblique to a central axis of the rod 120.

The driven surfaces 232a, 234a are effectively "open" to the proximal end 222, extending from the connecting lateral edges 246, 248, respectively. For example, the first driven surface 232a is effectively bounded by the first connecting lateral edge 246, a first outer longitudinal edge 250 and a connecting longitudinal edge 252. The second driven surface 234a is effectively bounded by the second connecting lateral edge 248, a second outer longitudinal edge 254, and the connecting longitudinal edge 252. The connecting longitudinal edge 252 can be formed by or include a longitudinal groove. In other embodiments, the connecting longitudinal edge 252 can be substantially linear (i.e., within 5% of a truly linear corner or edge).

The adaptor male coupling portion 134 can also include or define opposing chamfer surfaces 260, 262 proximate the proximal end 222. The chamfer surfaces 260, 262 extend from a corresponding guide surface 264, 266 otherwise extending circumferentially between the interface structures 224a, 224b, and reflect a taper in outer diameter of the rod 120. The adaptor male coupling portion 134 can also include an optional axial retention feature in the form of a circumferential groove 270. The circumferential groove 270 is located distally away from the deflection surfaces 230a, 230b such that it interrupts the driven surfaces 232a, 234a of the first interface structure 224a, and the driven surfaces 232b, 234b of the second interface structure 224b. The axial retention feature can alternatively be one or more notches, flats, holes, troughs, a biased mechanism, etc. In other embodiments, the axial retention feature is omitted.

Figure 12:
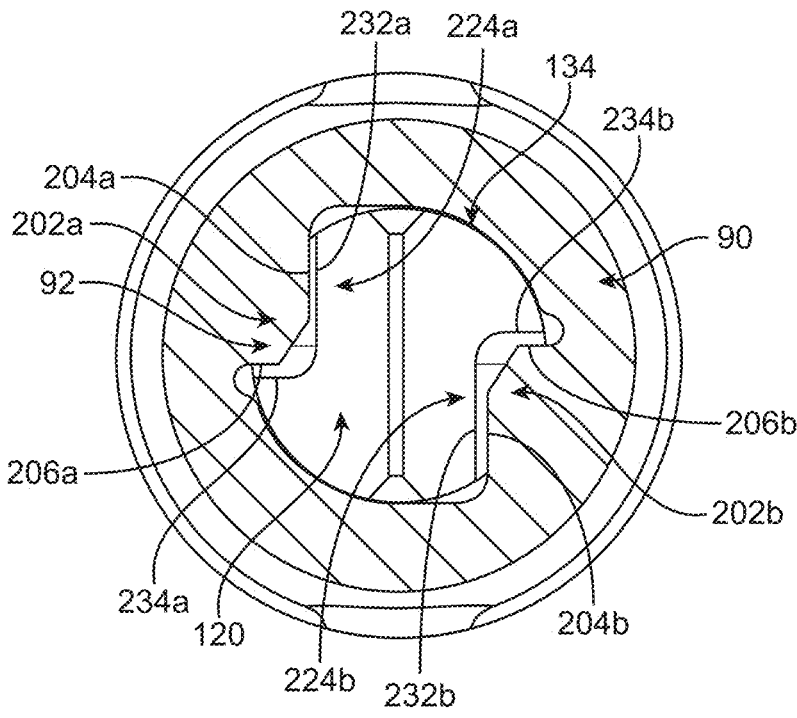
FIG. 12 is a simplified cross-section view the rod of FIG. 10 assembled to the drill chuck of FIG. 9.
Figure 13:
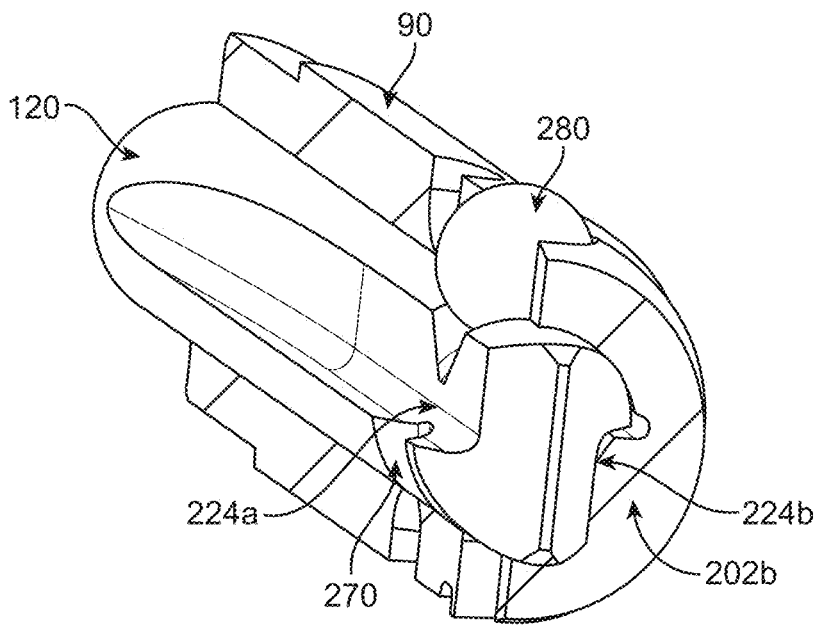
FIG. 13 is a perspective view of a portion of the assembly of FIG. 12.

Engagement between the adaptor male coupling portion 134 and the drill female coupling portion 92 upon insertion of the rod 120 into the drive chuck 90 is shown in FIGS. 12 and 13. The interface structures 224a, 224b of the adaptor male coupling portion 134 are aligned with a respective one of the drive pins 202a, 202b. For example, the first driven surface 232a of the first interface structure 224a is aligned with or slidingly contacts the first drive surface 204a of the first drive pin 202a, and the second driven surface 234a is aligned with or slidingly contacts the second drive surface 206a. In a similar manner, the first and second driven surfaces 232b, 234b of the second interface structure 224b are aligned with the first and second drive surfaces 204b, 206b, respectively, of the second drive pin 202b. FIG. 13 further reflects that in some optional embodiments, one or more balls 280 (or other axial retention member) can be maintained by the drive chuck 90 and arranged to engage the circumferential groove 270 of the rod 120, effectuating an axial lock of the rod 120 relative to the drive chuck 90. Regardless, a driven interface is established between the drive chuck 90 and the rod 120. An input torque at the drive chuck 90 is transferred to the rod 120 at the interface structures 224a, 224b. Rotation of the drive chuck 90 in a first direction (clockwise relative to an orientation of FIGS. 11 and 12) transfers a rotational force or torque onto the rod 120 at the interface between the first drive surface 204a of the first drive pin 202a and the first driven surface 232a of the first interface structure 224a, as well as at the interface between the first drive surface 204b of the second drive pin 202b and the first driven surface 232b of the second interface structure 224b. Rotation of the drive chuck 90 in an opposite, second direction (counterclockwise) transfers a rotational force or torque onto the rod 120 at the interface between the second drive surface 206a of the first drive pin 202a and the second driven surface 234a of the first interface structure 224a, as well as at the interface between the second drive surface 206b of the second drive pin 202b and the second driven surface 234b of the second interface structure 224b.

The adaptor male coupling structures of the present disclosure are not limited to the exemplary configuration of the adaptor male coupling structure 134. In more general terms, any configuration that is complementary to the configuration of the drill female coupling structure provided with the powered handpiece in question (that may or may not be akin to the drill female coupling structure 92 described above) is acceptable.

Returning to FIG. 6, a format of the adaptor female coupling portion 156 can be selected in accordance with any known, or in the future developed, tool male coupling portion 106. As a point of reference, most conventional surgical cutting tools generally include the shaft 100 forming or carrying the cutting head 102 opposite the tang 104 that otherwise forms or carries the tool male coupling portion 106. The shaft 100 can be formed of a rigid, surgically safe material (e.g., stainless steel), and defines opposing, first and second (or distal and proximal) ends 300, 302. The cutting head or dissection portion 102 is provided (formed or assembled) adjacent the distal end 300. The cutting head 102 can assume a wide variety of forms appropriate for performing a desired rotary surgical cutting procedure (e.g., cutting, debulking, resecting, dissecting, or removing anatomical tissue including bone). By way of one non-limiting embodiment, the cutting head 102 can be a bur having any shape, size, flute pattern, etc., as desired. While the elongated shaft 100 is illustrated as being linear or straight, in other embodiments the shaft 100 can define one or more longitudinal bends or curves; in related embodiments, surgical cutting tools of the present disclosure can further include an outer sleeve (not shown) that supports a curved version of the shaft 100 as the shaft 100 is rotated.

The tang 104 and the tool male coupling portion 106 formed or carried thereby can assume a variety of configurations. In this regard, a format of the tang 104 is in no way limited by the present disclosure. Virtually any design, currently known or in the future developed, appropriate for establishing a coupled connection with a collet or the like in a manner that facilitates driven rotation of the surgical cutting tool 84 with rotation of the collet are available. Thus, the coupling features provided by the tool male coupling portion 106 can include one or more of a perimeter shape (e.g., cylindrical, tapered, etc.) of the tang 104, surface indentations (e.g., grooves, slots, etc.), surface projections or protrusions (e.g., flanges, bumps, etc.), one or more auxiliary components carried by the tang 104 (e.g., a biased ball), etc. Regardless of an exact design, the adaptor female coupling portion 156 is formatted to provide a complementary construction.

Figure 14:
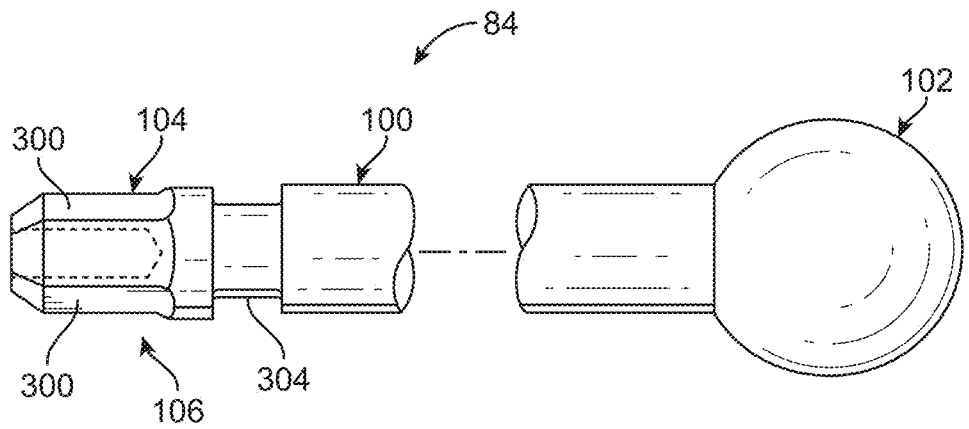
FIG. 14 is a side view of an example surgical cutting instrument useful with the adaptor assemblies of the present disclosure and illustrating an example tool male coupling portion.

By way of further explanation, one possible construction of the surgical cutting tool 84 is shown in FIG. 14. The cutting tool 84 includes the elongated shaft 100, the cutting head 102, and the tang 104 otherwise forming or providing the tool male coupling portion 106 (referenced generally). The tool male coupling portion 106 includes a plurality of driven surfaces 300. The driven surfaces 300 are substantially planar and extend in substantially parallel alignment with the longitudinal axis of the cutting tool 84. As further shown in FIG. 15 (that otherwise illustrates an engaged state between the cutting tool 84 and the collet 150), the driven surfaces 300 are formed in a substantially hexagonal pattern to define driving corners 302 between each driven surface 300. Alternatively, the tool male coupling portion 106 may have eight, four, three, etc., of the drive surfaces. With some cutting tools, an annular groove 304 can be formed along the tang 104; with these and related embodiments, a locking ball or the like (not shown) can be included with the adaptor assembly 80 (FIG. 4) for providing an axial lock with the cutting tool 84 at the annular grove. Regardless, and as shown in FIG. 15, the adaptor female coupling portion 156 (referenced generally) is configured to engage the so-configured tool make coupling portion 106 upon insertion of the tang 104 into the collet 150. For example, the adaptor female coupling portion 156 can include drive surfaces 306 sized and shaped to interface with a corresponding one of the driven surfaces 300. The drive surfaces 306 may or may not have the convex shape illustrated in FIG. 15. As the tang 104 is inserted into the collet 150, the driven surfaces 300 slidingly contact or abut a corresponding one of the drive surfaces 306. In the engaged state of FIG. 15, driven rotation of the collet 150 transfers a rotational force or torque onto the cutting tool 84 at the interface between each of the drive surfaces 306 and the driven surfaces 300.

Figure 15:
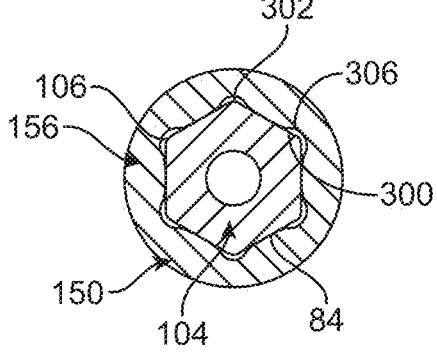
FIG. 15 is a simplified cross-sectional view of the surgical cutting instrument of FIG. 14 assembled to an adaptor assembly of the present disclosure, including engagement between the tool male coupling portion of the surgical cutting tool and an example adaptor female coupling portion of the adaptor assembly.

It will be understood that the tool male coupling portion 106 represented by FIG. 14, and thus the adaptor female coupling portion 156 represented by FIG. 15, is but one example in accordance with principles of the present disclosure. Surgical cutting tools useful with the present disclosure can have a plethora of other tool male coupling portion designs. The adaptor female coupling portions of the present disclosure can thus also have a number of other configurations that may or may not be implicated by FIG. 15. In more general terms, any female coupling portion format compatible with the tool male coupling portion of a surgical cutting tool of interest can be employed.

The surgical systems and adaptor assemblies of the present disclosure provide a marked improvement over previous designs. The adaptor assemblies facilitate use of a variety of different rotary-type surgical cutting tools with a powered handpiece or drill that is not otherwise compatible with a coupling format embodied by the cutting tool.

Although the present disclosure has been described with reference to preferred embodiments, workers skilled in the art will recognize that changes can be made in form and detail without departing from the spirit and scope of the present disclosure.

What is claimed is:

1. A surgical system for cutting tissue, the system comprising:
   a powered handpiece including:
      a housing,
      a drive chuck rotatably maintained by the housing and providing a drill female coupling portion;
   a surgical cutting tool including:
      a shaft defining opposing, first and second ends,
      a cutting head provided adjacent the first end,
      a tang provided adjacent the second end and providing a tool male coupling portion;
   an adaptor assembly including:
      a rod defining a proximal region opposite a distal region, wherein the proximal region provides an adaptor male coupling portion configured to engage the drill female coupling portion,
      a collet defining a trailing region opposite a leading region, wherein the leading region provides an adaptor female coupling portion configured to engage the tool male coupling portion,
      wherein the distal region of the rod and the trailing region of the collet form complementary engagement features for coupling the rod to the collet, the complementary engagement features including drive surfaces arranged to slidingly contact corresponding driven surfaces,
      an enclosure rotatably maintaining the collet;
   wherein a format of the tool male coupling portion differs from a format of the drill female coupling portion such that the tool male coupling portion is incompatible with the drill female coupling portion; and wherein upon final assembly of the rod to the collet, driven rotation of the drive chuck is transferred to the surgical cutting tool by the adaptor assembly.

2. The surgical system of claim 1, wherein the complementary engagement features are configured to transfer torque directly from the rod to the collet during operation.

3. The surgical system of claim 1, wherein the complementary engagement features are configured for axial assembly of the rod to the collet.

4. The surgical system of claim 1, wherein the enclosure includes a distal end region having a bore sized to rotationally support the shaft of the surgical cutting tool during operation.

5. The surgical system of claim 1, wherein the enclosure includes one or more bearing assemblies for rotatably supporting the collet.

6. The surgical system of claim 1, wherein the adaptor assembly comprises a conversion device and a drive device, the conversion device including the rod and the drive device including the collet.

7. The surgical system of claim 1, wherein the adaptor assembly is configured such that the rod and collet are assembled in an axial direction relative to a longitudinal axis of the collet.

8. The surgical system of claim 1, wherein the enclosure is configured to support a curved shaft of a surgical cutting tool.

9. The surgical system of claim 1, wherein the adaptor assembly is configured to provide an axial lock between the rod and the collet.

10. The surgical system of claim 1, wherein the adaptor assembly is configured to provide a rotational lock between the rod and the collet.

11. The surgical system of claim 1, wherein the adaptor assembly is configured to transfer rotational force in both clockwise and counterclockwise directions.

12. The surgical system of claim 1, wherein the adaptor assembly is configured to accommodate surgical cutting tools having an annular groove for axial locking.

* * * * *